United States Patent
Lee et al.

(10) Patent No.: US 10,017,608 B2
(45) Date of Patent: Jul. 10, 2018

(54) COPOLYCARBONATE AND METHOD FOR PREPARING THE SAME

(71) Applicant: LG CHEM, LTD., Seoul (KR)

(72) Inventors: Ki Jae Lee, Daejeon (KR); Young Wook Son, Daejeon (KR); Moo Ho Hong, Daejeon (KR); Hyong Minh Bahn, Daejeon (KR); Jung Jun Park, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/514,018

(22) PCT Filed: Aug. 17, 2016

(86) PCT No.: PCT/KR2016/009043
§ 371 (c)(1),
(2) Date: Mar. 24, 2017

(87) PCT Pub. No.: WO2017/039189
PCT Pub. Date: Mar. 9, 2017

(65) Prior Publication Data
US 2017/0298177 A1   Oct. 19, 2017

(30) Foreign Application Priority Data

Sep. 1, 2015 (KR) .................. 10-2015-0123707
Feb. 18, 2016 (KR) .................. 10-2016-0019091

(51) Int. Cl.
*C07C 323/52* (2006.01)
*C08G 64/08* (2006.01)
*C08G 64/24* (2006.01)

(52) U.S. Cl.
CPC .......... *C08G 64/081* (2013.01); *C07C 323/52* (2013.01); *C08G 64/24* (2013.01)

(58) Field of Classification Search
USPC .......................................................... 528/204
See application file for complete search history.

(56) References Cited

U.S. PATENT DOCUMENTS

| | | |
|---|---|---|
| 3,773,812 A | 11/1973 | Schutze et al. |
| 4,414,408 A | 11/1983 | Cottman |
| 4,448,950 A | 5/1984 | Baron et al. |
| 4,972,903 A | 5/1990 | Schreckenberg et al. |
| 5,037,937 A | 8/1991 | Komatsu et al. |
| 6,664,361 B2 | 12/2003 | Sasaki et al. |
| 7,691,304 B2 | 4/2010 | Agarwal et al. |
| 2003/0232957 A1 | 12/2003 | Silvi et al. |
| 2003/0236384 A1 | 12/2003 | Silvi et al. |
| 2005/0288407 A1 | 12/2005 | Heuer et al. |
| 2013/0267665 A1 | 10/2013 | Huggins et al. |

FOREIGN PATENT DOCUMENTS

| | | |
|---|---|---|
| JP | 0618997 B2 | 3/1994 |
| JP | 2556859 B2 | 11/1996 |
| JP | 2002-249472 A | 9/2002 |
| JP | 2008-274239 A | 11/2008 |
| JP | 2010-1432 A | 1/2010 |
| JP | 4740565 B2 | 8/2011 |
| JP | 5451119 B2 | 3/2014 |
| KR | 940005872 B1 | 6/1994 |
| KR | 1020050019744 A | 3/2005 |
| KR | 101260516 B1 | 5/2013 |
| KR | 101407514 B1 | 6/2014 |
| KR | 101491781 B1 | 2/2015 |
| KR | 1020150032174 A | 3/2015 |

*Primary Examiner* — Terressa Boykin
(74) *Attorney, Agent, or Firm* — Dentons US LLP

(57) ABSTRACT

Provided are a copolycarbonate having superior weather resistance as well as excellent mechanical properties, and a preparation method thereof.

8 Claims, 2 Drawing Sheets

[Fig. 1]
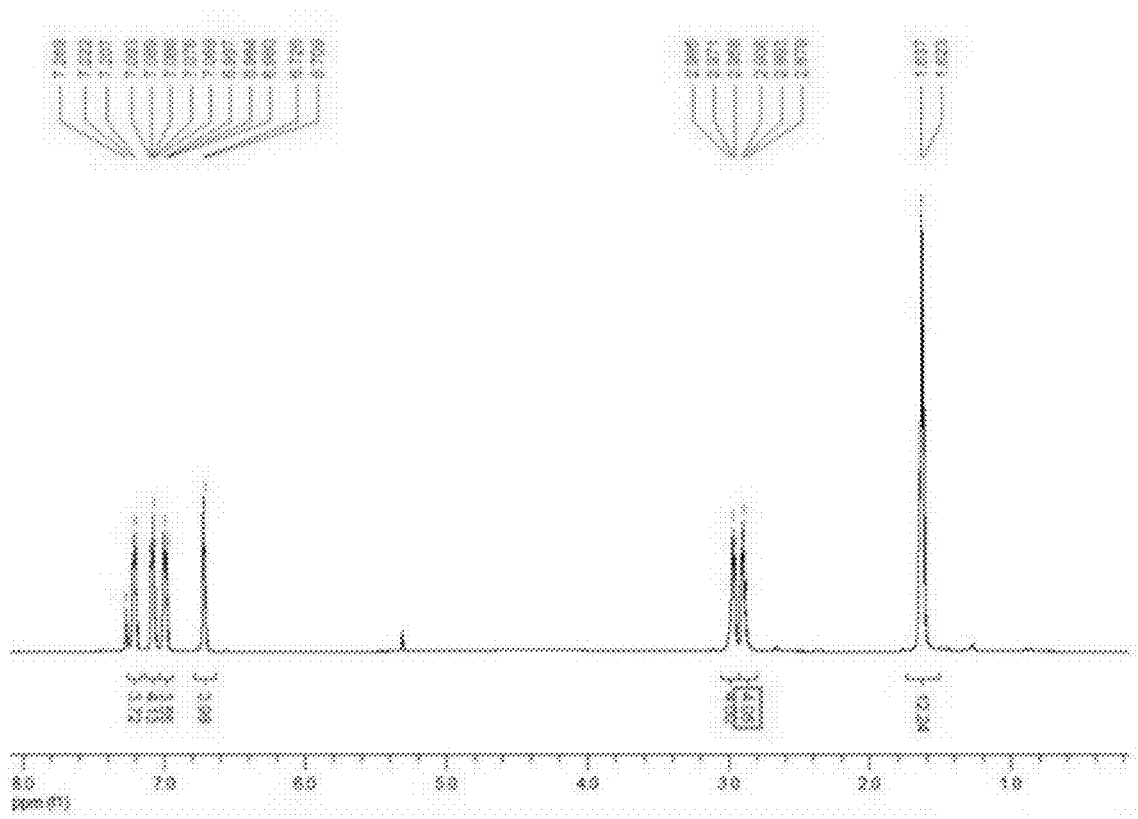

[Fig. 2]
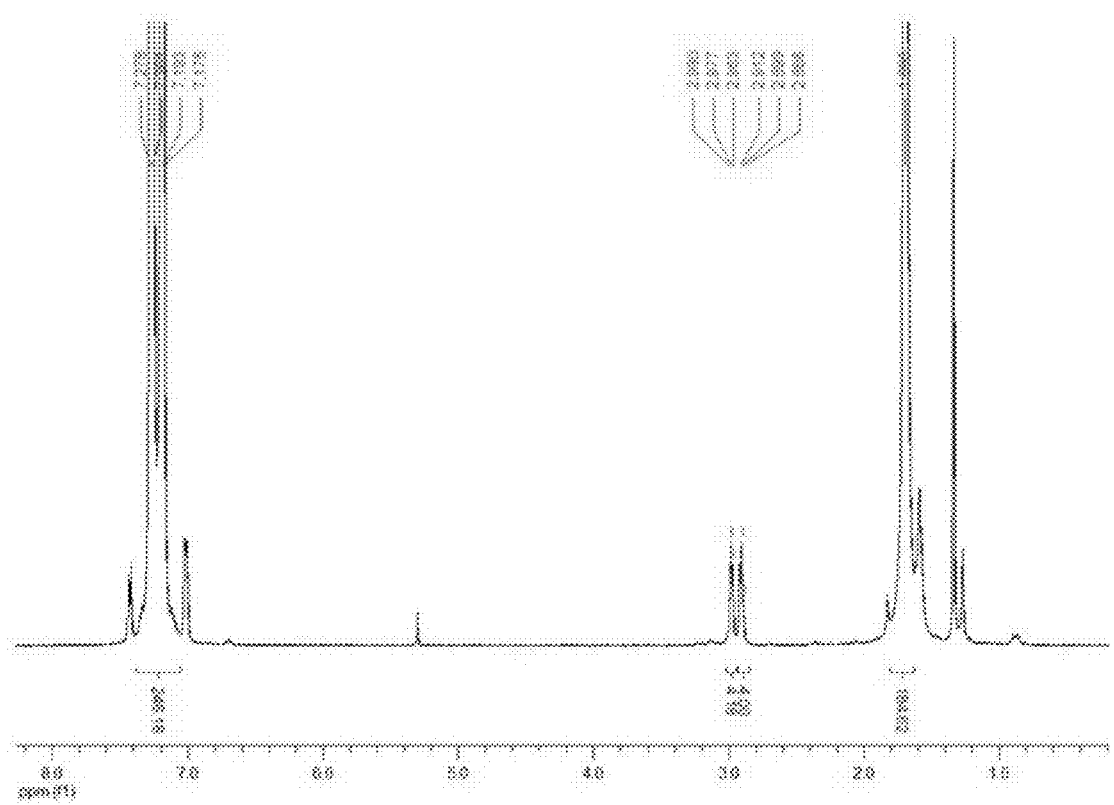

COPOLYCARBONATE AND METHOD FOR PREPARING THE SAME

CROSS REFERENCE TO RELATED APPLICATIONS

This application is a National Stage Entry of International Application No. PCT/KR2016/009043, filed Aug. 17, 2016, and claims the benefit of and priority to Korean Patent Application No. 10-2015-0123707, filed on Sep. 1, 2015 and Korean Patent Application No. 10-2016-0019091, filed on Feb. 18, 2016 with the Korean Intellectual Property Office, the disclosure of which is herein incorporated by reference in its entirety.

TECHNICAL FIELD

The present invention relates to a copolycarbonate having superior weather resistance as well as excellent mechanical properties, and a preparation method thereof.

BACKGROUND OF ART

A polycarbonate resin is a polymer material which is applied to a wide range of fields such as exterior materials of electrical and electronic products, automotive parts, construction materials, optical components, etc., due to their excellent physical properties such as impact strength, dimensional stability, heat resistance, transparency, etc.

With recent expansion of the application fields of the polycarbonate resin, there is a demand for a novel structure of copolycarbonate which has improved heat resistance and weather resistance while maintaining the intrinsic physical properties of the polycarbonate resin.

Accordingly, studies have been attempted to obtain desired properties by copolymerizing two or more aromatic diols having different structures to introduce a monomer having a different structure to a main chain of polycarbonate. However, most technologies have limitations that a production cost is high, and transparency is deteriorated when chemical resistance or impact strength is improved, and chemical resistance or impact strength is deteriorated when transparency is improved.

Accordingly, there is a need for the development of a novel structure of copolycarbonate having superior weather resistance while having excellent mechanical properties such as hardness, etc.

DETAILED DESCRIPTION OF THE INVENTION

Technical Problem

The present invention provides a copolycarbonate having superior weather resistance as well as excellent mechanical properties, and a preparation method thereof.

Technical Solution

The present invention provides a copolycarbonate having a weight average molecular weight of 1,000 to 100,000 g/mol, which includes a repeating unit represented by the following Chemical Formula 1 and a repeating unit represented by the following Chemical Formula 2.

Further, the present invention provides a preparation method of the copolycarbonate, including the step of polymerizing a composition including a compound represented by the following Chemical Formula 3, an aromatic diol compound, and a carbonate precursor.

Further, the present invention provides a molded article manufactured by using the copolycarbonate.

Hereinafter, a copolycarbonate, a preparation method thereof, and a molded article according to specific embodiments of the present invention will be described in more detail.

According to an embodiment of the present invention, provided is a copolycarbonate having a weight average molecular weight of 1,000 to 100,000 g/mol, which includes a repeating unit represented by the following Chemical Formula 1 and a repeating unit represented by the following Chemical Formula 2:

[Chemical Formula 1]

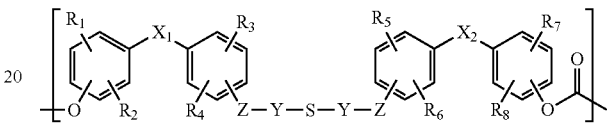

wherein $R_1$ to $R_8$ are each independently hydrogen or $C_{1-10}$ alkyl,
Y is $C_{1-10}$ alkylene,
Z is a bond, —OCO—, or —COO—, and
$X_1$ to $X_2$ are each independently $C_{1-10}$ alkylene unsubstituted or substituted with phenyl, $C_{3-15}$ cycloalkylene unsubstituted or substituted with $C_{1-10}$ alkyl, O, S, SO, $SO_2$, or CO,

[Chemical Formula 2]

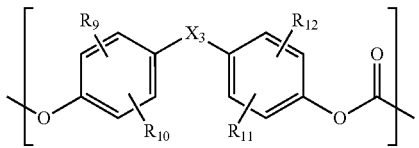

wherein $R_9$ to $R_{12}$ are each independently hydrogen, $C_{1-10}$ alkyl, $C_{1-10}$ alkoxy, or halogen, and
$X_3$ is $C_{1-10}$ alkylene unsubstituted or substituted with phenyl, $C_{3-15}$ cycloalkylene unsubstituted or substituted with $C_{1-10}$ alkyl, O, S, SO, $SO_2$, or CO.

Particularly, the copolycarbonate includes a functional group, in which alkyl chains are linked to a thio functional group as a center, thereby showing excellent flowability and weather resistance while having excellent impact resistance, transparency, and heat resistance which are intrinsic properties of the known polycarbonate.

In this regard, Y is preferably $C_{1-5}$ alkylene.

Further, $R_1$ to $R_8$ are preferably each independently hydrogen, or $C_{1-4}$ alkyl.

$R_9$ to $R_{12}$ are each independently hydrogen, methyl, chloro, or bromo. Further, $X_1$ to $X_3$ are preferably each independently linear or branched $C_{1-10}$ alkylene unsubstituted or substituted with phenyl, and more preferably, methylene, ethane-1,1-diyl, propane-2,2-diyl, butane-2,2-diyl, 1-phenylethane-1,1-diyl, or diphenylmethylene. More preferably, $X_1$ to $X_3$ are cyclohexane-1,1-diyl, O, S, SO, $SO_2$, or CO.

Further, a molar ratio of the repeating unit represented by Chemical Formula 1 and the repeating unit represented by Chemical Formula 2 may be 1:0.001 to 1:1, and preferably 1:0.001 to 1:0.3.

The repeating unit represented by Chemical Formula 1 has characteristics of having excellent flowability and weather resistance, and the repeating unit represented by Chemical Formula 2 has characteristics of having excellent transparency and impact resistance, and therefore, it is preferable that when these repeating units are included in the above molar ratio, the prepared copolycarbonate may exhibit superior mechanical properties, flowability, and weather resistance.

Further, the copolycarbonate may have a weight average molecular weight of 1,000 to 100,000 g/mol, preferably 10,000 to 100,000 g/mol, and more preferably, 10,000 to 40,000 g/mol.

Further, the copolycarbonate may have a change in yellow index (dYI) of 20 or less, preferably 1 to 15, and more preferably 3 to 13, as measured in accordance with ASTM G155.

Meanwhile, according to another embodiment of the present invention, provided is a preparation method of the copolycarbonate, including the step of polymerizing a composition including a compound represented by the following Chemical Formula 3, an aromatic diol compound, and a carbonate precursor:

[Chemical Formula 3]

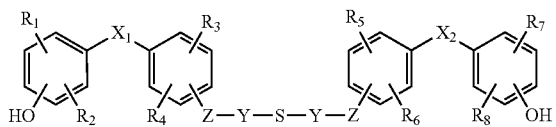

wherein $R_1$ to $R_8$ are each independently hydrogen or $C_{1-10}$ alkyl,

Y is $C_{1-10}$ alkylene,

Z is a bond, —OCO— or —COO—, and $X_1$ to $X_2$ are $C_{1-10}$ alkylene unsubstituted or substituted with phenyl, $C_{3-15}$ cycloalkylene unsubstituted or substituted with $C_{1-10}$ alkyl, O, S, SO, $SO_2$, or CO.

The aromatic diol compound is a compound represented by the following Chemical Formula 4, and corresponds to Chemical Formula 2:

[Chemical Formula 4]

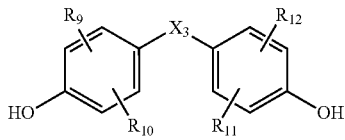

wherein $X_3$ and $R_9$ to $R_{12}$ are the same as those defined in Chemical Formula 2.

Specific examples of the aromatic diol compound may include one or more compounds selected from the group consisting of bis(4-hydroxyphenyl)methane, bis(4-hydroxyphenyl)ether, bis(4-hydroxyphenyl)sulfone, bis(4-hydroxyphenyl)sulfoxide, bis(4-hydroxyphenyl) sulphide, bis(4-hydroxyphenyl)ketone, 1,1-bis(4-hydroxyphenyl)ethane, 2,2-bis(4-hydroxyphenyl)propane (bisphenol A), 2,2-bis(4-hydroxyphenyl)butane, 1,1-bis(4-hydroxyphenyl)cyclohexane(bisphenol Z), 2,2-bis(4-hydroxy-3,5-dibromophenyl)propane, 2,2-bis(4-hydroxy-3,5-dichlorophenyl)propane, 2,2-bis(4-hydroxy-3-bromophenyl)propane, 2,2-bis(4-hydroxy-3-chlorophenyl)propane, 2,2-bis(4-hydroxy-3-methylphenyl)propane, 2,2-bis(4-hydroxy-3,5-dimethylphenyl)propane and 1,1-bis(4-hydroxyphenyl)-1-phenylethane.

The carbonate precursor functions to link the compound represented by Chemical Formula 3 with the compound represented by Chemical Formula 4, and specific examples thereof may include phosgene, triphosgene, diphosgene, bromophosgene, dimethyl carbonate, diethyl carbonate, dibutyl carbonate, dicyclohexyl carbonate, diphenyl carbonate, ditolyl carbonate, bis(chlorophenyl) carbonate, m-cresyl carbonate, dinaphthyl carbonate, bis(diphenyl) carbonate, or bishaloformate.

Upon the polymerization, the compound represented by Chemical Formula 3 may be used in an amount of 0.1% by weight or more, 1% by weight or more, or 3% by weight or more, and 20% by weight or less, 10% by weight or less, or 7% by weight or less, based on 100% by weight of the composition.

Further, the aromatic diol compound may be used in an amount of 40% by weight or more, 50% by weight or more, or 55% by weight or more, and 80% by weight or less, 70% by weight or less, or 65% by weight, based on 100% by weight of the composition.

Further, the carbonate precursor may be used in an amount of 10% by weight or more, 20% by weight or more, or 30% by weight, and 60% by weight or less, 50% by weight or less, or 40% by weight or less, based on 100% by weight of the composition.

In this regard, the polymerization may be preferably performed by interfacial polymerization, and upon interfacial polymerization, the polymerization reaction is possible at low temperature under normal pressure, and it is easy to control the molecular weight.

The polymerization temperature is preferably 0° C. to 40° C., and the reaction time is preferably 10 minutes to 5 hours. Further, it is preferred that pH is maintained at 9 or higher or at 11 or higher during reaction.

The solvent usable in the polymerization is not particularly limited, as long as it is a solvent usually used in the polymerization of copolycarbonate in the art, and for example, halogenated hydrocarbons such as methylene chloride, chlorobenzene, etc.

Further, the polymerization is preferably performed in the presence of an acid binder, and the acid binder may be alkali metal hydroxides such as sodium hydroxide, potassium hydroxide, etc., or an amine compound such as pyridine, etc.

Further, the polymerization is preferably performed in the presence of a molecular weight controller in order to control the molecular weight of copolycarbonate upon polymerization. As the molecular weight controller, $C_{1-20}$ alkylphenol may be used. Specific examples thereof may include p-tert-butylphenol, p-cumylphenol, decylphenol, dodecylphenol, tetradecylphenol, hexadecylphenol, octadecylphenol, eicosylphenol, docosylphenol, or triacontylphenol. The molecular weight controller may be injected before initiation of the polymerization, during initiation of the polymerization, or after initiation of the polymerization. The molecular weight controller may be, for example, included in an amount of 0.01 to 10 parts by weight, and preferably, 0.1 to 6 parts by weight, based on 100 parts by weight of the aromatic diol compound. Within this range, a desired molecular weight may be obtained.

Further, to promote the polymerization reaction, a reaction promoter, for example, a tertiary amine compound such as triethylamine, tetra-n-butylammoniumbromide tetra-n- butylphosphoniumbromide, etc., a quaternary ammonium compound, a quaternary phosphonium compound may be further used.

According to still another embodiment of the present invention, provided is a molded article manufactured by using the copolycarbonate. As describe above, the copolycarbonate including the repeating unit represented by Chemical Formula 1 has improved weather resistance while having excellent mechanical properties, and therefore, the molded article may be applied to a variety of fields, compared to molded articles manufactured by using the previous copolycarbonate.

The molded article may further include, if necessary, one or more selected from the group consisting of an antioxidant, a plasticizer, an antistatic agent, a nucleating agent, a flame retardant, a lubricant, an impact modifier, an optical brightener, an ultraviolet absorber, a pigment and a dye, in addition to the copolycarbonate according to the present invention.

A method of manufacturing the molded article may include, for example, the steps of mixing the copolycarbonate of the present invention and other additive using a mixer, extrusion-molding the mixture with an extruder to prepare a pellet, drying the pellet, and then injecting the pellet with an injection molding machine.

BRIEF DESCRIPTION OF DRAWINGS

FIG. 1 is a $^1$H-NMR graph of a compound prepared in Example 1; and
FIG. 2 is a $^1$H-NMR graph of a copolycarbonate prepared in Example 1.

ADVANTAGEOUS EFFECTS

According to the present invention, provided are a copolycarbonate having superior weather resistance as well as excellent mechanical properties, and a preparation method thereof.

DETAILED DESCRIPTION OF THE EMBODIMENTS

The present invention will be described in more detail with reference to the following Examples. However, the following Examples are for illustrative purposes only, and the disclosure of the present invention is not intended to be limited by the following Examples.

EXAMPLE: PREPARATION OF COPOLYCARBONATE

Example 1

(1) Preparation of Bis-(4-(2-(4-Hydroxyphenyl) Propan-2-yl)Phenyl)3,3'-Thiodipropionate In a round-bottom flask, 5 g of 3,3'-thiodipropionic acid was dissolved in 50 ml of methylene chloride solvent, and then 7.47 g of oxalyl chloride and 0.001 g of DMF were added dropwise thereto at room temperature, followed by stirring at room temperature for 4 hours. The solvent was removed using a rotary evaporator to obtain 3,3-thiodipropionic chloride. Thereafter, the obtained 3,3'-thiodipropionic chloride was dissolved in 50 ml of dichloromethane without a purification process, and slowly added to 13.12 g of bisphenol A, 2.3 g of NaOH, and 50 ml of water, followed by stirring at room temperature for 24 hours. 50 ml of HCl was added to terminate the reaction, and the reaction product was washed with water and dichloromethane. A final compound, bis-(4-(2-(4-hydroxyphenyl)propan-2-yl)phenyl)3,3'-thiodipropionate was obtained in a final yield of 85%.

$^1$H-NMR of the compound is shown in FIG. 1.

(2) Preparation of Copolycarbonate Resin

To a 2-L main reactor equipped with a nitrogen purge device and a condenser and enabling maintenance at room temperature using a circulator, 620 g of water, 116.24 g of BPA, 0.6 g of bis-(4-(2-(4-hydroxyphenyl)propan-2-yl)phenyl)3,3'-thiodipropionate prepared in (1), 102.5 g of NaOH, and 200 ml of MeCl$_2$ were injected, followed by stirring for a few minutes.

After stopping the nitrogen purge, 62 g of triphosgene and 120 g of MeCl$_2$ were added to a 1-L round-bottom flask to dissolve triphosgene. Then, the dissolved triphosgene solution was slowly injected to the main reactor where the BPA solution was dissolved. After completion of injection, 2.28 g of PTBP(p-tert-butylphenol) was added, followed by stirring for about 10 minutes. After completion of stirring, 97 g of 40% wt NaOH aqueous solution was added and 1.16 g of TEA as a coupling agent was added thereto. At this time, a reaction pH was maintained at 11~13. After the reaction solution was allowed to stand for a time for sufficient reaction, pH was decreased to 3~4 by addition of HCl to terminate the reaction. After stopping the stirring, a polymer layer and an aqueous layer were separated and then the aqueous layer was removed, and the residue was repeatedly washed with pure H$_2$O again, and this washing process was repeated 3 to 5 times.

After completion of washing, only the polymer layer was extracted, and the polymer crystals were obtained by re-precipitation using a non-solvent of methanol, H$_2$O or the like. In this regard, a weight average molecular weight of the prepared polycarbonate was 31,000 g/mol.

$^1$H-NMR of the prepared copolycarbonate is shown in FIG. 2.

Example 2

A polycarbonate was prepared in the same manner as in Example 1, except that 115.5 g of BPA was used, and 2.4 g of bis-(4-(2-(4-hydroxyphenyl)propan-2-yl)phenyl)3,3'-thiodipropionate was used.

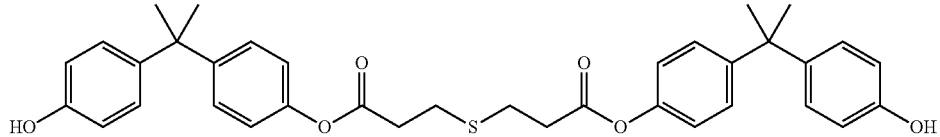 [SMILES: CC(C)(c1ccc(O)cc1)c1ccc(OC(=O)CCSCCC(=O)Oc2ccc(C(C)(C)c3ccc(O)cc3)cc2)cc1]

Example 3

A polycarbonate was prepared in the same manner as in Example 1, except that 114.2 g of BPA was used, and 5.8 g of bis-(4-(2-(4-hydroxyphenyl)propan-2-yl)phenyl)3,3'-thiodipropionate was used.

Example 4

A polycarbonate was prepared in the same manner as in Example 1, except that 111.6 g of BPA was used, and 12.6 g of bis-(4-(2-(4-hydroxyphenyl)propan-2-yl)phenyl)3,3'-thiodipropionate was used.

Example 5

A polycarbonate was prepared in the same manner as in Example 1, except that 1.97 g of PTBP was used.

Example 6

A polycarbonate was prepared in the same manner as in Example 1, except that 3.41 g of PTBP was used.

Comparative Example 1

A polycarbonate was prepared in the same manner as in Example 1, except that 116.47 g of BPA was used without using bis-(4-(2-(4-hydroxyphenyl)propan-2-yl)phenyl)3,3'-thiodipropionate.

Comparative Example 2

A polycarbonate was prepared in the same manner as in Example 1, except that 116.47 g of BPA was used and 1.97 g of PTBP was used without using bis-(4-(2-(4-hydroxyphenyl)propan-2-yl)phenyl)3,3'-thiodipropionate.

Comparative Example 3

A polycarbonate was prepared in the same manner as in Example 1, except that 116.47 g of BPA was used and 3.41 g of PTBP was used without using bis-(4-(2-(4-hydroxyphenyl)propan-2-yl)phenyl)3,3'-thiodipropionate.

Experimental Example: Evaluation of Physical Properties of Copolycarbonate

The properties of the extrusion samples of the polycarbonates prepared in Example 1 and Comparative Example 1 were measured by the following method. The results are given in the following Table 1.

Weight average molecular weight (g/mol): measured by weighing with PC standard using Agilent 1200 series.
Flowability (MI): measured according to ASTM D1238 (under conditions of 300° C. and 1.2 kg).
Glass transition temperature (Tg, ° C.): Differential Scanning calorimetry (DSC).
Impact strength (IMP, J/m): measured according to ASTM D256(⅛ inch, Notched Izod) at 23° C.
Weather resistance (dYI, 500 time): a change in yellow index (dYI) of the sample was measured using a Zenon Whether 0 meter according to ASTM G155.

TABLE 1

| | Molecular weight (g/mol) | MI (g/10 min) | Tg (° C.) | IMP (J/m) | DYI |
|---|---|---|---|---|---|
| Example 1 | 31,000 | 12.7 | 151.1 | 790 | 11 |
| Example 2 | 31,000 | 15 | 150.8 | 782 | 9 |
| Example 3 | 31,000 | 16.2 | 151.2 | 766 | 8 |
| Example 4 | 31,000 | 17.5 | 151.3 | 746 | 7 |
| Example 5 | 34,900 | 7.2 | 151.5 | 852 | 11 |
| Example 6 | 24,700 | 28.6 | 151.6 | 641 | 11 |
| Comparative Example 1 | 31,000 | 10.8 | 151 | 784 | 24 |
| Comparative Example 2 | 34,900 | 5.7 | 151.8 | 870 | 23 |
| Comparative Example 3 | 24,700 | 26.2 | 151.2 | 645 | 25 |

Referring to Table 1, it was confirmed that the copolycarbonate prepared in Example 1 has impact strength equivalent to that of a general polycarbonate of Comparative Example 1, and also has very excellent flowability.

Further, the copolycarbonates of Examples have superior weather resistance which is a property of withstanding various weathers while maintaining the intrinsic physical properties of polycarbonate resin, thereby being easily applied to various fields such as exterior materials of electrical and electronic products, vehicle components, and construction materials.

The invention claimed is:

1. A copolycarbonate, comprising a repeating unit represented by the following Chemical Formula 1 and a repeating unit represented by the following Chemical Formula 2, and having a weight average molecular weight of 1,000 to 100,000 g/mol:

[Chemical Formula 1]

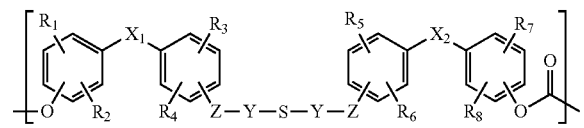

wherein $R_1$ to $R_8$ are each independently hydrogen or $C_{1-10}$ alkyl,
Y is $C_{1-10}$ alkylene,
Z is a bond, —OCO—, or —COO—, and
$X_1$ to $X_2$ are each independently $C_{1-10}$ alkylene unsubstituted or substituted with phenyl, $C_{3-15}$ cycloalkylene unsubstituted or substituted with $C_{1-10}$ alkyl, O, S, SO, $SO_2$, or CO,

[Chemical Formula 2]

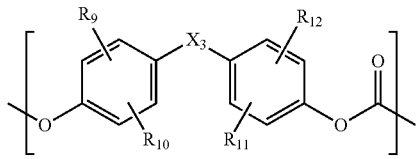

wherein $R_9$ to $R_{12}$ are each independently hydrogen, $C_{1-10}$ alkyl, $C_{1-10}$ alkoxy, or halogen, and
$X_3$ is $C_{1-10}$ alkylene unsubstituted or substituted with phenyl, $C_{3-15}$ cycloalkylene unsubstituted or substituted with $C_{1-10}$ alkyl, O, S, SO, $SO_2$, or CO.

2. The copolycarbonate of claim 1, wherein Y is $C_{1-5}$ alkylene.

3. The copolycarbonate of claim 1, wherein $R_1$ to $R_8$ are each independently hydrogen or $C_{1-4}$ alkyl.

4. The copolycarbonate of claim 1, wherein a molar ratio of the repeating unit represented by Chemical Formula 1 and the repeating unit represented by Chemical Formula 2 is 1:0.001 to 1:1.

5. The copolycarbonate of claim 1, wherein a change in yellow index (dYI) is 20 or less, as measured in accordance with ASTM G155.

6. A preparation method of the copolycarbonate of claim 1, the method comprising the step of polymerizing a composition comprising a compound represented by the following Chemical Formula 3, an aromatic diol compound, and a carbonate precursor:

[Chemical Formula 3]

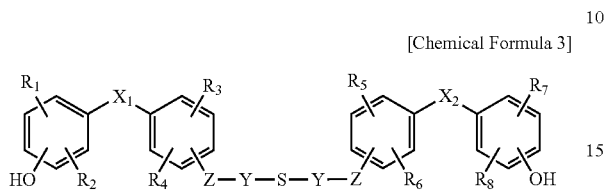

wherein $R_1$ to $R_8$ are each independently hydrogen or $C_{1-10}$ alkyl,

Y is $C_{1-10}$ alkylene,

Z is a bond, —OCO—, or —COO—, and $X_1$ to $X_2$ are $C_{1-10}$ alkylene unsubstituted or substituted with phenyl, $C_{3-15}$ cycloalkylene unsubstituted or substituted with $C_{1-10}$ alkyl, O, S, SO, $SO_2$, or CO.

7. The preparation method of claim 6, wherein the compound represented by Chemical Formula 3 is used in an amount of 0.1% by weight or more and 20% by weight or less, based on 100% by weight of the composition.

8. A molded article manufactured by using the copolycarbonate of claim 1.

* * * * *